(12) United States Patent
Vaccaro

(10) Patent No.: US 7,467,052 B2
(45) Date of Patent: Dec. 16, 2008

(54) SYSTEMS AND METHODS FOR DETECTING DISCONTINUOUS FIBERS IN COMPOSITE LAMINATES

(76) Inventor: Christopher M. Vaccaro, 735 Sunset Hills Dr., O'Fallon, MO (US) 63366

( * ) Notice: Subject to any disclaimer, the term of this patent is extended or adjusted under 35 U.S.C. 154(b) by 0 days.

(21) Appl. No.: 11/271,529

(22) Filed: Nov. 10, 2005

(65) Prior Publication Data

US 2007/0118313 A1    May 24, 2007

(51) Int. Cl.
G01R 13/00    (2006.01)
G06F 19/00    (2006.01)

(52) U.S. Cl. ........................................ 702/66
(58) Field of Classification Search .................. 702/66
See application file for complete search history.

(56) References Cited

U.S. PATENT DOCUMENTS

| | | | |
|---|---|---|---|
| 4,258,573 A | | 3/1981 | Fontaine |
| 4,457,174 A | * | 7/1984 | Bar-Cohen et al. ............ 73/598 |
| 4,592,237 A | | 6/1986 | Ogura et al. |
| 4,848,159 A | | 7/1989 | Kennedy et al. |
| 4,875,372 A | | 10/1989 | Gilbert |
| 4,944,185 A | | 7/1990 | Clark, Jr. et al. |
| 4,947,351 A | * | 8/1990 | Moran et al. .................. 702/39 |
| 5,031,458 A | | 7/1991 | Young et al. |
| 5,118,464 A | | 6/1992 | Richardson et al. |
| 5,372,043 A | | 12/1994 | Speight, II et al. |
| 5,554,808 A | * | 9/1996 | Chiao .......................... 73/598 |
| 6,041,020 A | | 3/2000 | Caron et al. |
| 6,220,099 B1 | | 4/2001 | Marti et al. |
| 6,234,025 B1 | * | 5/2001 | Gieske et al. ................. 73/642 |
| 6,484,583 B1 | | 11/2002 | Chennell et al. |
| 6,532,820 B1 | | 3/2003 | Fleming et al. |
| 6,591,679 B2 | * | 7/2003 | Kenefick et al. .............. 73/597 |
| 2003/0023393 A1 | * | 1/2003 | Oravecz ....................... 702/39 |
| 2003/0145655 A1 | | 8/2003 | Lorraine et al. |
| 2008/0000299 A1 | * | 1/2008 | Georgeson ................... 73/606 |

OTHER PUBLICATIONS

"FlawInspecta, High Speed Low-Cost Ultrasonic Inspection and Imaging", NDT Solutions, Inc., 3 pages.
Hillger, "Ultrasonic Imaging of Defects in Concrete Components by Pulse-Echo-Technique", pp. 1-4, Braunschweig, Germany.
Roach, Dorrell, Kollgaard, Dreher, "Optimizing Composite Inspections", 5 pages, available at www.sae.org/aeromag/features/optimizing_comp/ and retrieved Oct. 27, 2005.
PCT Search Report and Written Opinion for PCT application No. PCT/US2006/043744 mailed on May 4, 2007.

* cited by examiner

Primary Examiner—Michael P. Nghiem
Assistant Examiner—Cindy H Khuu

(57) ABSTRACT

Systems and methods for detecting discontinuous fibers in composite laminates are disclosed. In one embodiment, a method includes transmitting an incident ultrasonic signal onto a front surface of a composite laminate at a plurality of locations over an area of interest, receiving a full waveform at each of the plurality of locations over the area of interest, storing the full waveform at each of the plurality of locations over the area of interest, and analyzing the full waveform at each of the plurality of locations over the area of interest for an amplitude distortion indicative of a fiber discontinuity within the composite laminate, including selecting a gate value corresponding to a depth location within the composite laminate and displaying a C-scan image of an amplitude value from the full waveform at the plurality of locations over the area of interest.

19 Claims, 6 Drawing Sheets

SYSTEMS AND METHODS FOR DETECTING DISCONTINUOUS FIBERS IN COMPOSITE LAMINATES

TECHNICAL FIELD

The present disclosure relates to systems and methods for inspecting composite laminates, and more specifically, to improved systems and methods for detecting discontinuous fibers in composite laminates.

BACKGROUND

Composite laminates with discontinuous fibers (i.e. wrinkles) may be undesirable. Wrinkles that cause physical indentations on the surface of a laminate may be easily detected using visual methods. Wrinkles that occur internal to the composite laminate, however, may not be easy to detect due to the normal surface appearance produced during the manufacturing and cure cycle. In this case, there may be typically no indication that the structure has discontinuous fibers.

A variety of systems and methods are known for inspecting composite materials using ultrasound. Such systems include, for example those pulse-echo systems generally disclosed in U.S. Pat. No. 6,874,365 B2 issued to Deveney et al, U.S. Pat. No. 6,041,020 issued to Caron et al., and U.S. Pat. No. 5,118,464 issued to Richardson et al., as well as those through-transmission systems generally disclosed in U.S. Pat. No. 6,484,583 B1 issued to Chennell et al. and U.S. Pat. No. 5,372,043 issued to Speight et al. Although desirable results have been achieved using such prior art systems, improved systems for detecting discontinuous fibers in composite laminates would have utility.

SUMMARY

The disclosure is directed to systems and methods for detecting discontinuous fibers in composite laminates. In one embodiment, a method of performing an ultrasonic inspection of a composite laminate includes transmitting an incident ultrasonic signal onto a front surface of the composite laminate at a plurality of locations over an area of interest, receiving a full waveform at each of the plurality of locations over the area of interest, storing the full waveform at each of the plurality of locations over the area of interest, and analyzing the full waveform at each of the plurality of locations over the area of interest for an amplitude distortion indicative of a fiber discontinuity within the composite laminate, including selecting a gate value corresponding to a depth location within the composite laminate and displaying a C-scan image of an amplitude value from the full waveform at the plurality of locations over the area of interest.

BRIEF DESCRIPTION OF THE DRAWINGS

The disclosed embodiments are described in detail below with reference to the following drawings.

DETAILED DESCRIPTION

The present disclosure relates to systems and methods for detecting discontinuous fibers in composite laminates. Many specific details of certain embodiments are set forth in the following description and in FIGS. 1-7 to provide a thorough understanding of such embodiments. However, additional embodiments may be practiced without one or more of the details described below.

In general, the disclosed embodiments may detect discontinuous fibers in composite laminates using ultrasonic signals and a software gating process that enables interrogation of the laminate at discrete depths. More specifically, the disclosed embodiments may start by collecting a full RF ultrasonic waveform for the composite laminate under inspection. The RF waveform may then be post-processed to produce a series of images that evaluates the RF signal amplitude at each layer within the composite laminate. An amplitude of the signal response at each layer indicates whether the signal is from the fibers within the laminate or from the thin layer of resin between plies within the laminate. At any given depth within the laminate where fiber distortion exists, the signal response may produce high and low amplitude values. In one particular embodiment, the high and low amplitude values of the signal response produce a Moray pattern in the C-scan data, as described more fully below.

Figure 1:
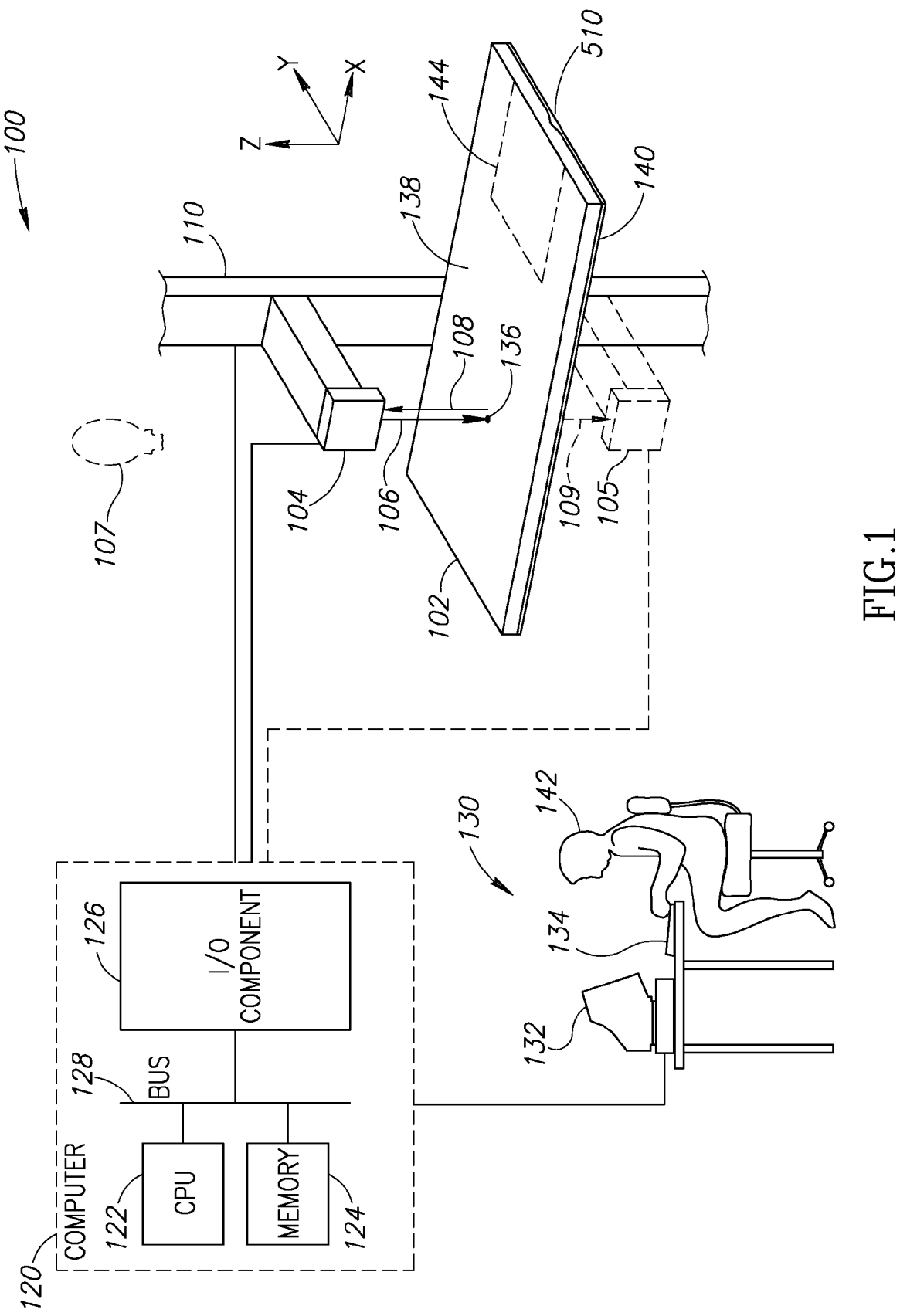
FIG. 1 is a schematic view of an ultrasonic inspection system in accordance with one embodiment.

FIG. 1 is a schematic view of an ultrasonic inspection system 100 adapted to perform ultrasonic inspections of a composite laminate (or workpiece) 102 in accordance with one embodiment. In this embodiment, the system 100 includes an ultrasonic sensor 104 adapted to transmit an incident ultrasonic signal 106 onto the composite laminate 102, and to receive a reflected ultrasonic signal 108 that is reflected back from the composite laminate 102 in a pulse-echo mode of operation. The system 100 may further include an auxiliary ultrasonic sensor 105 positioned opposite from the sensor 104 and adapted to receive a transmitted ultrasonic signal 109 (in a through-transmission mode of operation), which is a portion of the incident ultrasonic signal 106 that passes through the composite laminate 102.

The ultrasonic sensor 104 (and auxiliary ultrasonic sensor 105) may be coupled to a position control device 110 and to a data acquisition and control system 120. The position control device 110 is adapted to provide position control of the ultrasonic sensor 104 (and the auxiliary ultrasonic sensor 105) along the x, y, and z axes, and may be used to perform point measurements or x-y scanning measurements over the composite laminate 102. In one particular embodiment, the ultrasonic system 100 may include one or more hardware components commercially-available from UTEX Scientific Instruments, Inc. of Mississagua, Ontario, Canada.

As shown in FIG. 1, in this embodiment, the data acquisition and control system 120 includes a central processing unit (CPU) 122 and a memory component 124. The memory component 124 may include one or more memory modules, such as Random Access Memory (RAM) modules, Read Only Memory (ROM) modules, Dynamic Random Access Memory (DRAM) modules, and any other suitable memory modules. The data acquisition and control system 120 also includes an input/output (I/O) component 126 that may include a variety of known I/O devices, including network connections, video and graphics cards, disk drives or other computer-readable media drives, displays, or any other suitable I/O modules. A data bus 128 operatively couples the CPU 122, the memory component 124, and the I/O component 126. The data acquisition and control system 120 is operatively coupled to a control component 130 having a monitor 132 and a command input device 134 (e.g. a keyboard, an audio-visual input device, etc.).

Figure 2:
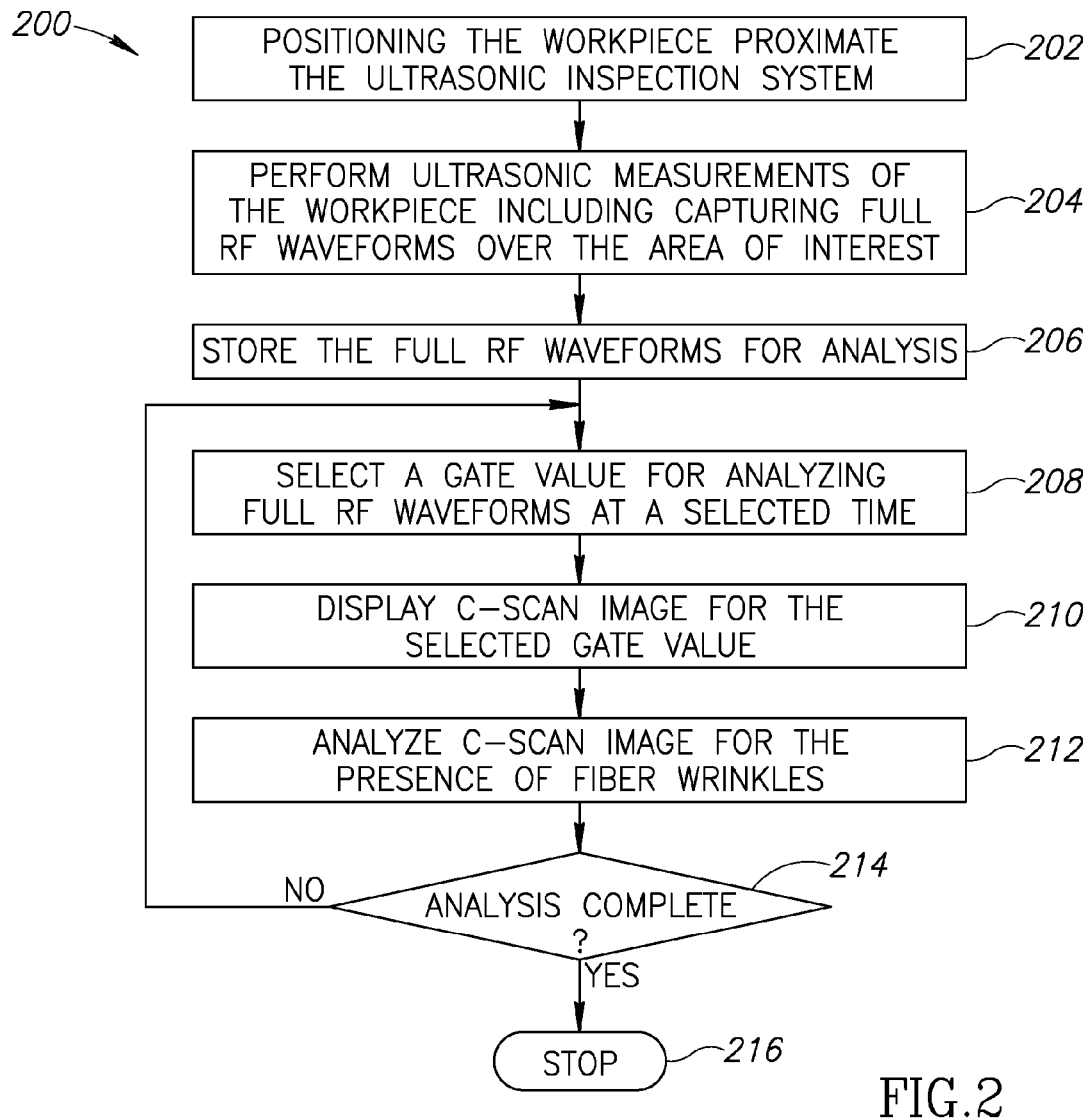
FIG. 2 is a flow chart showing a method of performing ultrasonic inspections in accordance with another embodiment.

FIG. 2 is a flow chart showing a method 200 of performing ultrasonic inspections of the composite laminate 102 using the system 100 in accordance with another embodiment. In this embodiment, the method 200 includes positioning the composite laminate 102 proximate the ultrasonic inspection system 100 at a block 202. In alternate embodiments, the composite laminate 102 and ultrasonic sensor 104 (and auxiliary ultrasonic sensor 105) are immersed in a liquid medium using an immersion tank, or may include a squirter system. In a further embodiment, the system 100 may include a contact transducer (e.g. a contact portable C-scan system) coupled to the position control device 110 wherein the incident ultrasonic signals 106 are coupled into the composite laminate 102 using a thin layer of water. Next, at a block 204, ultrasonic measurements of the composite laminate 102 are performed, including capturing full RF waveforms over an area of interest (e.g. over all or only part of the composite laminate 102).

Figure 3:
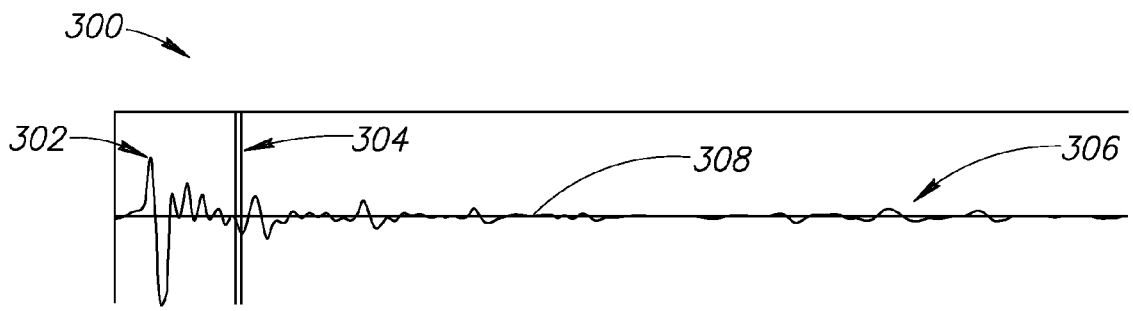
FIG. 3 is graph showing a representative full RF waveform and a representative gate period in accordance with one embodiment.

FIG. 3 shows a representative full RF waveform 300 (amplitude versus time) at a particular x-y location 136 (FIG. 1) that is captured at block 204 of the method 200 (FIG. 2). As shown in FIG. 3, the full (or entire) RF waveform 300 of the reflected ultrasonic signals 108 is captured by the ultrasonic sensor 104 (or alternately, by a separate receiver 107 operatively positioned relative to the ultrasonic sensor 104 to receive the reflected ultrasonic signals 108), including as the incident signal 106 encounters a front surface 138 of the composite laminate 102, causing a front wall amplitude perturbation 302 in the full RF waveform 300. The full RF waveform 300 continues through to a back surface 140 of the composite laminate 102 (FIG. 1), and may be indicated by a back wall amplitude perturbation 306 in the full RF waveform 300. As noted above, the full RF waveform 300 may be recorded by the ultrasonic sensor 104, or by a separate receiver 107 (FIG. 1), capturing reflected ultrasonic signals 108 in the pulse-echo mode of operation. The full RF waveform shown in FIG. 3 is for a single point 136 over the composite laminate 102. A collection of such waveforms is used to produce a C-scan image of the area of interest of the composite laminate 102.

As further shown in FIG. 2, at a block 208, an operator 142 (FIG. 1) may select a gate value 304 (FIG. 3) for analyzing the full RF waveforms 300 at a selected time, and the amplitude values over the area of interest are displayed as a C-scan image for the selected gate value at a block 210. The selected gate value 304 corresponds to a particular depth along the z axis (FIG. 1) within the composite laminate 102.

Figure 4:
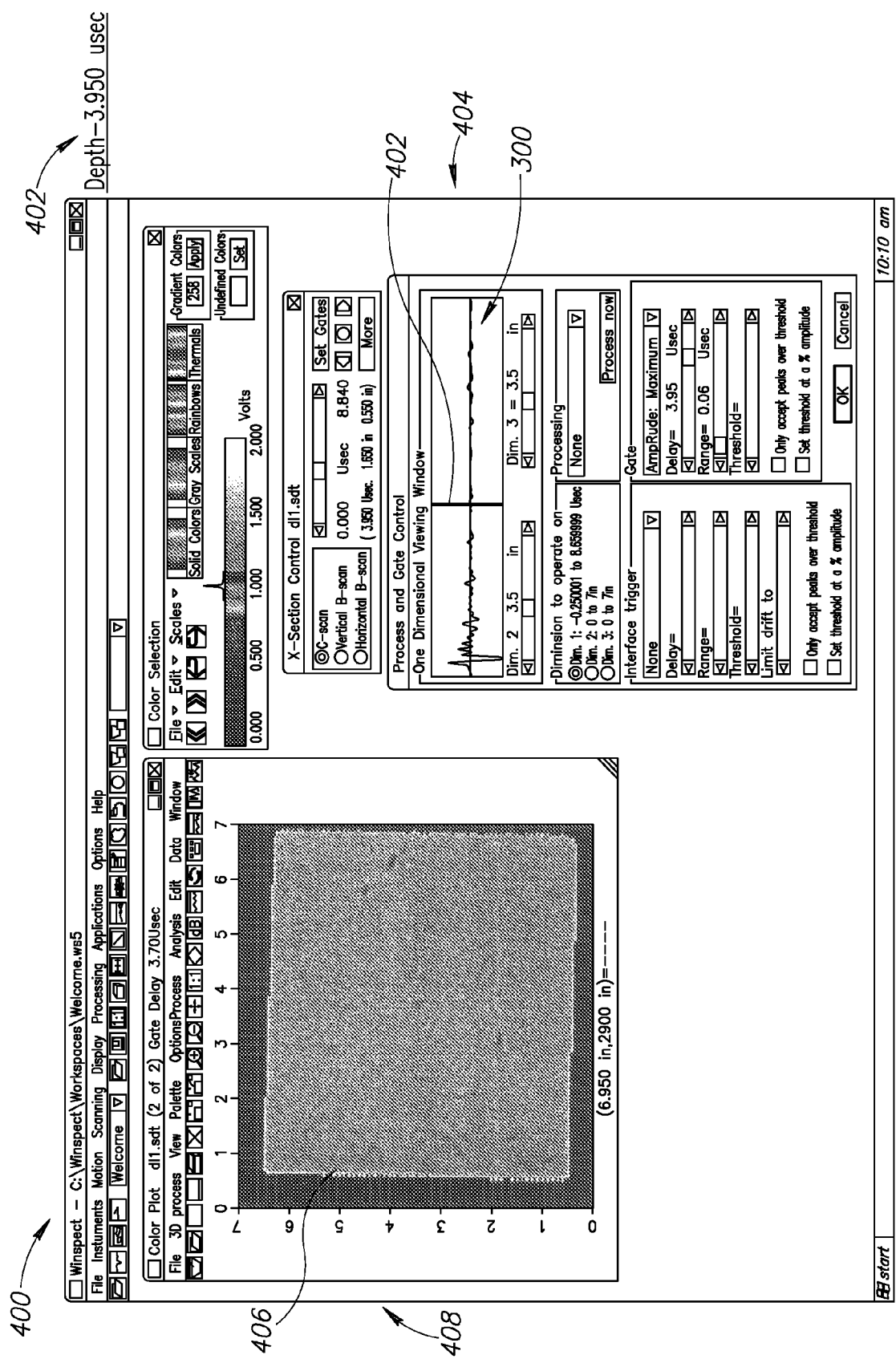
FIGS. 4 through 7 are C-scan images of a workpiece at different gate times obtained using a method in accordance with a further embodiment.

More specifically, FIG. 4 is a screen shot 400 shown on the display 132 by the data acquisition and control system 120 for a first gate value 402. The relative position of the first gate value 402 within the full RF waveform 300 is depicted in a first display portion 404 of the screen shot 400. A corresponding first C-scan image 406 of an area of interest 144 (FIG. 1) is depicted in a second display portion 408 of the screen shot 400. In this embodiment, the relatively uniform amplitudes shown in the first C-scan image 406 are indicative of the absence of any fiber wrinkles within the composite laminate 102.

In general, in samples without wrinkles (or other inconsistencies, such as foreign material or delaminations), the amplitude response between the front and back surfaces 138, 140 typically appears as low-level noise, as depicted in the first C-scan image 406 shown in FIG. 4. If a wrinkle exists, it would typically appear on a C-scan as having both high and low amplitude, however, the overall amplitude fluctuation is very low. Thus, for creating the C-scan images for analysis for wrinkles, a relatively narrow amplitude threshold may be set for reviewing the data. For example, in one particular embodiment, a method and system in accordance with the disclosure uses a gate width of 0.006 micro-seconds, and a maximum length of the full RF waveform 300 of 8.840 micro-seconds, over a six inch by six inch area of interest.

In one particular embodiment, the incident ultrasonic signal 106 has a frequency of approximately 1.0 MHz, however, in alternate embodiments, the incident ultrasonic signal 106 may have a frequency within the range of approximately 0.1 MHz to 10 MHz, depending upon a variety of factors, including the material characteristics of the composite laminate 102. Of course, any other suitable frequencies of the incident ultrasonic signal 106 may be used. In addition, in some embodiments, the frequency bandwidth of the incident ultrasonic signal 106 may be adjusted to be a relatively broadband frequency bandwidth (e.g. approximately ±5%), however, in alternate embodiments, larger or smaller frequency bandwidths may be used.

Figure 5:
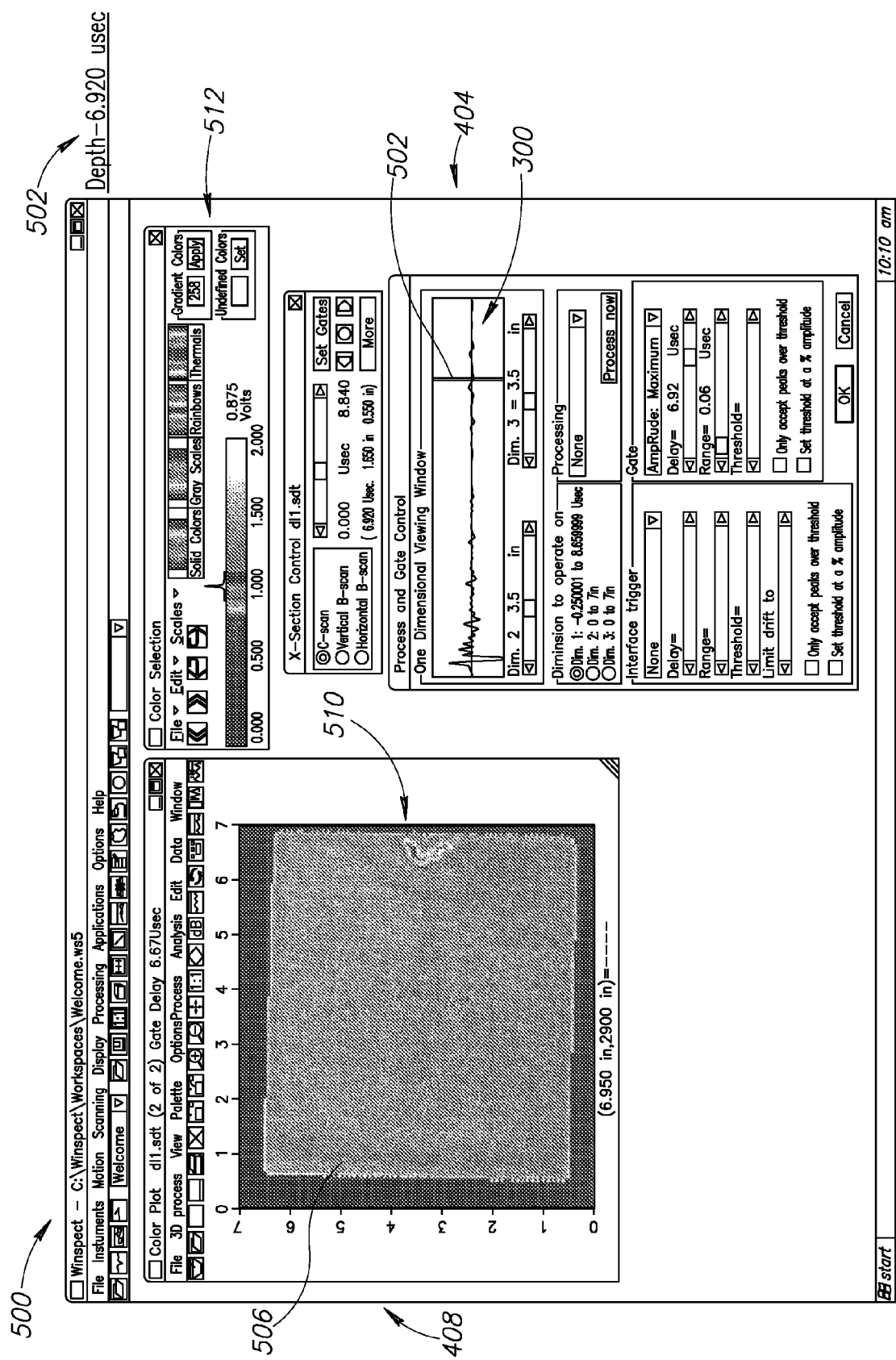
Figure 6:
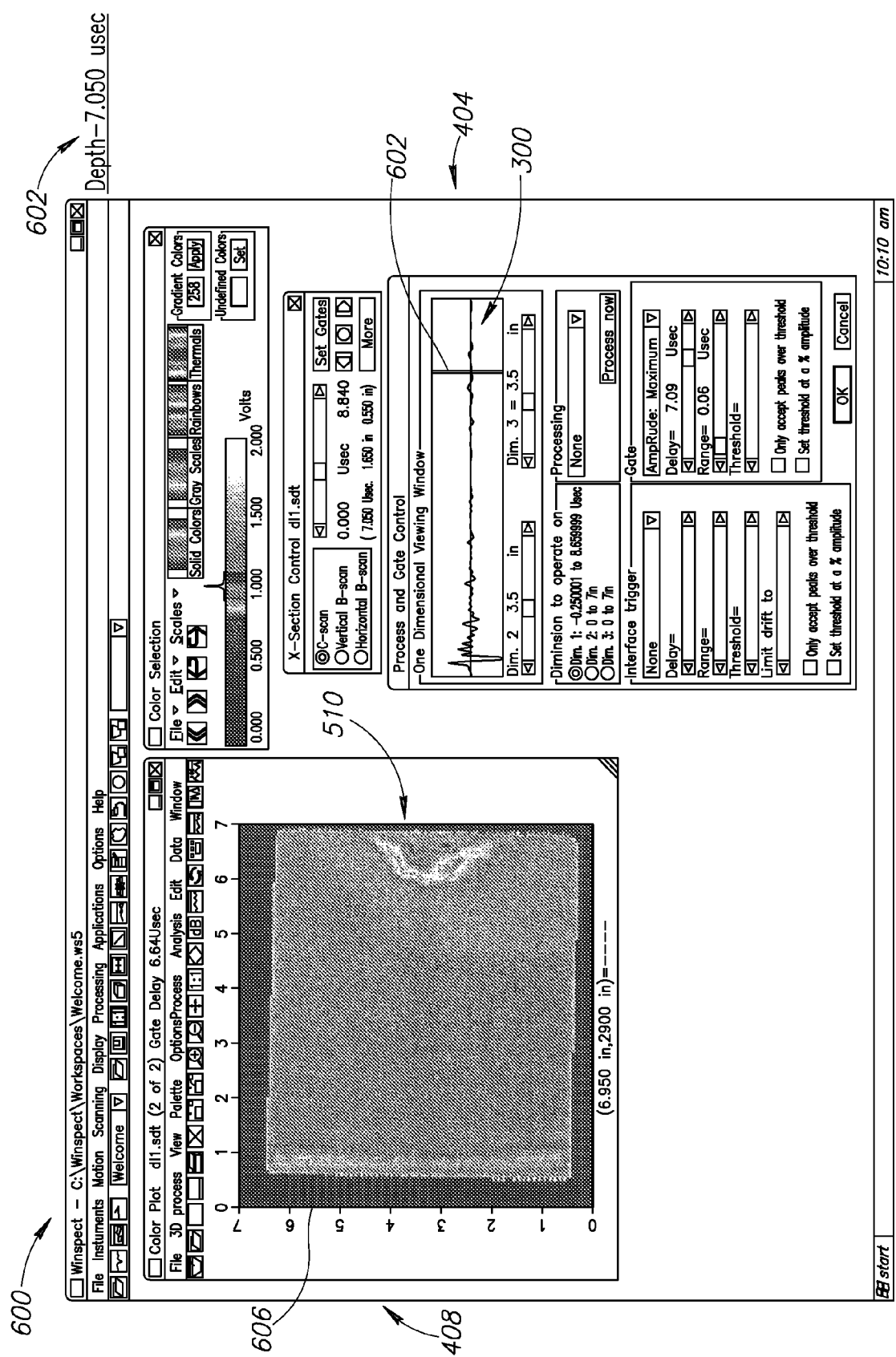
Figure 7:
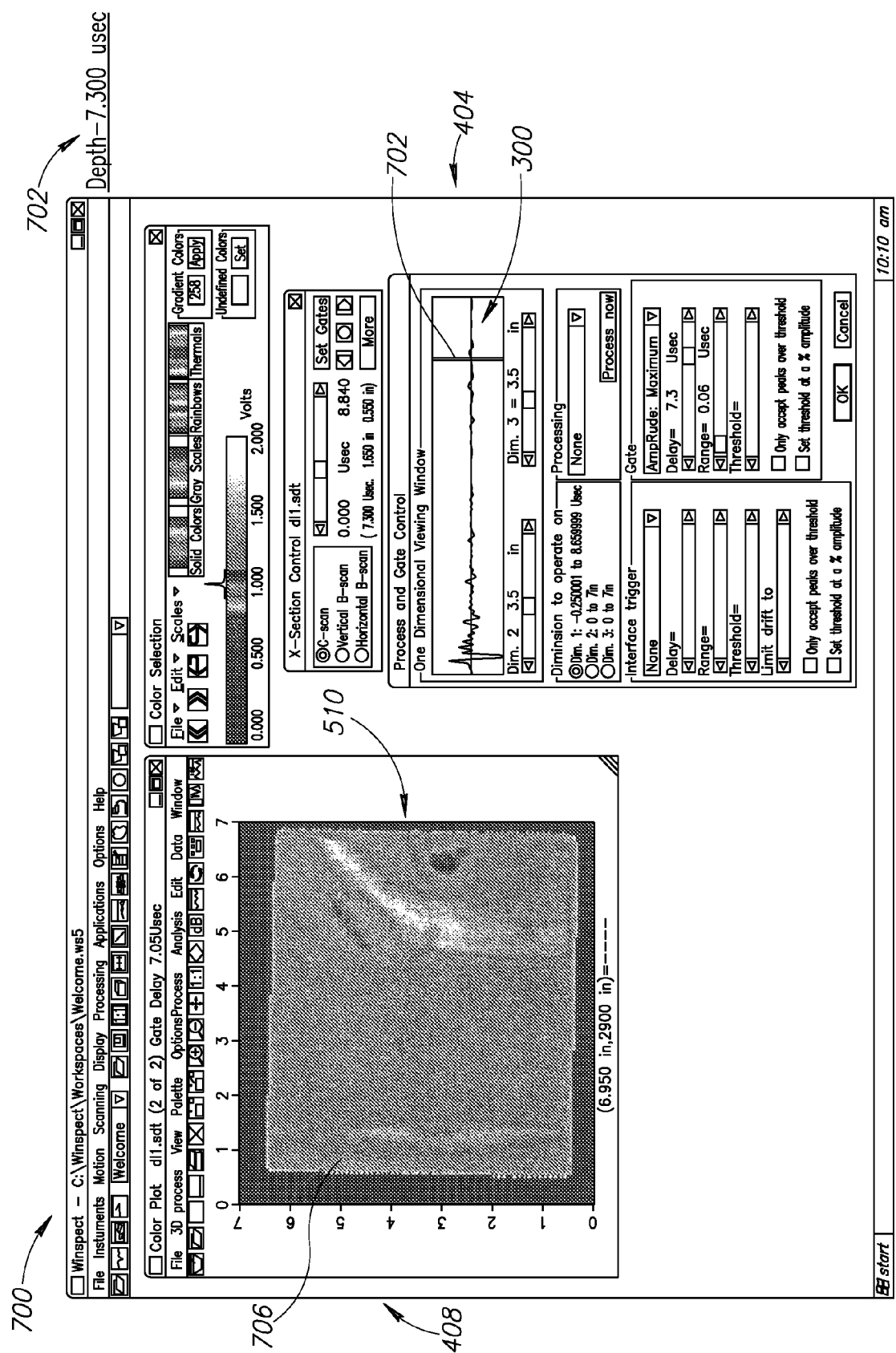

Referring again to FIG. 2, the method 200 further includes determining whether the analysis of the area of interest is complete at a block 214. If the analysis is not complete, the method 200 returns to block 208 for selection of another gate value, and blocks 208 through 212 are repeated. For example, FIGS. 5 through 7 show screen shots 500, 600, 700 including second, third, and fourth C-scan images 506, 606, 706 corresponding to second, third, and fourth gate values 502, 602, 702. At the second gate value 502 shown in FIG. 5, the second C-scan image 506 shows the amplitude distortions (also called Moray patterns) indicative of a fiber wrinkle 510 within the composite laminate 102 (also see FIG. 1).

It will be appreciated that the amplitudes of the RF waveform 300 at depths within the laminate may be relatively low compared to the amplitude perturbations 302, 306 caused by the front wall 138 and back wall 140 of the composite laminate 102. These low amplitudes may need to be enhanced in order to produce the sensitivity necessary to detect wrinkles in the composite laminate 102. In one particular embodiment, this enhancement is accomplished by adjusting (e.g. reducing) a color palette range 512 over a baseline RF signal 308 (FIG. 3). For example, in the embodiment shown in FIG. 5, the color palette range 512 was selectively adjusted (e.g. reduced) to capture amplitude differences of approximately a couple of dB.

Similarly, at the third and fourth gate values 602, 702, the third and fourth C-scan images 606, 706 also show amplitude distortions indicative of the fiber wrinkle 510 within the composite laminate 102. In this way, the amplitude signals may be mapped along the z axis through the composite laminate 102. In a particular embodiment, one or more portions of the method 200 may be automated to enable the C-scan images to be displayed in succession (e.g. as a movie) starting at the front surface 138 and continuing through the composite laminate 102 to the back surface 140. After the analysis of the area of interest is complete (block 214), the method 200 is terminated at a block 206.

Referring again to FIG. 1, in one aspect, a machine-readable medium may be used to store a set of machine-readable instructions (e.g. a computer program or software product) into the data acquisition and control system 120, wherein the machine-readable instructions embody a method of performing ultrasonic inspections for detecting fiber wrinkles in composite laminates in accordance with the disclosure. The machine-readable medium may be any type of medium which can store data that is readable by the data acquisition and control system 120, including, for example, a floppy disk, CD ROM, optical storage disk, magnetic tape, flash memory card, digital video disk, RAM, ROM, or any other suitable storage medium. The machine-readable medium, or the instructions stored thereon, may be temporarily or permanently installed in any desired component of the data acquisition and control system 120, including, for example, the I/O component 126, the memory component 124, and in one or more other portions of the data acquisition and control system 120 and the control component 130. Alternately, the machine-readable instructions may be implemented directly into one or more components of the data acquisition and control system 120 and the control component 130, without the assistance of the machine-readable medium.

In operation, the data acquisition and control system 120 is adapted to perform a method of performing ultrasonic inspections of a composite laminate in accordance with the disclosure. For example, the operator 142 may input one or more control signals that cause the system 100 to scan the area of interest 144 and store the full RF waveform data from the area of interest 144 into the memory component 124. The operator 142 may then transmit a command which causes the CPU 122 to invoke the software product to automatically perform one or more of the acts described above without further action or intervention by the operator 142. More specifically, the data acquisition and control system 120 may invoke a set of software instructions (e.g. stored in the memory component 126) that causes the CPU 122 to perform one or more aspects of a method of performing ultrasonic inspections. Alternately, one or more aspects of the various processes described above may be implemented in the data acquisition and control system 120 using any suitable programmable or semi-programmable hardware components (e.g. EPROM components).

Embodiments of methods and systems for detecting wrinkles within composite laminates in accordance with the disclosure may provide advantages over the prior art. Using Planer Peak Amplitude Mapping (described above) and a gating method which enables an operator to step through the RF waveform data through the depth of the composite laminate 102, may enable improved analysis, detection, and characterization of fiber discontinuities (or wrinkles) in comparison with the prior art. More specifically, prior art systems typically monitor a backwall signal via a gate which produces a C-scan image that measures the total energy loss of the incident ultrasonic signals 106 after it passes through the composite laminate 102. Disclosed embodiments, however, enable the operator to efficiently analyze the amplitude response at specific or predefined depths within the composite laminate.

While preferred and alternate embodiments have been illustrated and described, as noted above, many changes can be made without departing from the spirit and scope of the disclosure. Accordingly, the scope of the disclosure is not limited by the disclosured embodiments. Instead, the scope of the disclosure should be determined entirely by reference to the claims that follow.

What is claimed is:

1. A method of performing an ultrasonic inspection of a composite laminate, comprising:

transmitting an incident ultrasonic signal onto a front surface of the composite laminate at a plurality of locations over an area of interest;

receiving a full waveform at each of the plurality of locations over the area of interest;

storing the full waveform at each of the plurality of locations over the area of interest; and analyzing the full waveform at each of the plurality of locations over the area of interest for an amplitude distortion indicative of a fiber wrinkle within the composite laminate, including selecting a gate value corresponding to a depth location within the composite laminate and displaying a C-scan image of an amplitude value from the full waveform at the plurality of locations over the area of interest, wherein the composite laminate further includes a back surface opposite from the front surface, and wherein receiving a full waveform at each of the plurality of locations over the area of interest includes receiving a full waveform of amplitude versus time between the front and back surfaces of the composite laminate at each of the plurality of locations over the area of interest.

2. The method of claim 1, wherein transmitting an incident ultrasonic signal onto a front surface includes transmitting an incident ultrasonic signal onto a front surface using a first ultrasonic sensor, and wherein receiving a full waveform at each of the plurality of locations includes receiving a full waveform using the first ultrasonic sensor in a pulse-echo mode of operation.

3. The method of claim 1, wherein transmitting an incident ultrasonic signal onto a front surface includes transmitting an incident ultrasonic signal onto a front surface using a first ultrasonic sensor, and wherein receiving a full waveform at each of the plurality of locations includes receiving a full waveform using a second ultrasonic sensor operatively positioned relative to the first ultrasonic sensor in a pulse-echo mode of operation.

4. The method of claim 1, wherein storing the full waveform at each of the plurality of locations over the area of interest includes electronically storing the full waveform at each of the plurality of locations over the area of interest in a memory component of a data acquisition system.

5. The method of claim 1, wherein selecting a gate value corresponding to a depth location within the composite laminate includes selecting a gate value having a width of approximately 0.006 microseconds.

6. The method of claim 1, wherein analyzing the full waveform at each of the plurality of locations over the area of interest for an amplitude distortion indicative of a fiber wrinkle includes selectively adjusting a color palette range of the C-scan image over a baseline RF signal to capture amplitude differences of approximately a couple of dB.

7. The method of claim 1, wherein analyzing the full waveform at each of the plurality of locations over the area of interest includes mapping the composite component by selecting a plurality of gate values corresponding to a plurality of depth locations within the composite laminate.

8. The method of claim 1, wherein transmitting an incident ultrasonic signal onto a front surface of the composite laminate includes transmitting an incident ultrasonic signal through a layer of liquid using at least one of an immersion tank, a squirter system, and a contact transducer.

9. A system for performing an ultrasonic inspection of a composite laminate, comprising:

a sensor assembly including a first component adapted to transmit an incident ultrasonic signal onto a front surface of the composite laminate at a plurality of locations over an area of interest, and a second component adapted to receive a full waveform at each of the plurality of locations over the area of interest; and a data acquisition and control component operatively coupled to the sensor assembly and adapted to store the full waveform at each of the plurality of locations over the area of interest and further adapted to enable analysis of the full waveform at each of the plurality of locations over the area of interest for an amplitude distortion indicative of a fiber wrinkle within the composite laminate, wherein the analysis includes selecting a gate value corresponding to a depth location within the composite laminate and displaying a C-scan image of an amplitude value from the full waveform at the plurality of locations over the area of interest, wherein the composite laminate further includes a back surface opposite from the front surface, and wherein receiving a full waveform at each of the plurality of locations over the area of interest includes receiving a full waveform of amplitude versus time between the front and back surfaces of the composite laminate at each of the plurality of locations over the area of interest.

10. The system of claim 9, wherein the second component is at least one of co-located with and operatively positioned proximate to the first component.

11. The system of claim 9, wherein the sensor assembly is adapted to transmit a relatively broadband ultrasonic signal.

12. The system of claim 9, wherein the sensor assembly is adapted to transmit an incident ultrasonic signal having a frequency value in the range of approximately 0.1 MHz to approximately 10 MHz, inclusive.

13. The system of claim 9, wherein the control component is adapted to enable analysis of the full waveform at each of the plurality of locations over the area of interest for an amplitude distortion indicative of a fiber wrinkle within the composite laminate, wherein the analysis includes selectively adjusting a color palette range of the C-scan image over a baseline RF signal to capture amplitude differences of approximately a couple of dB.

14. The system of claim 9, wherein the control component is adapted to enable analysis of the full waveform at each of the plurality of locations over the area of interest for an amplitude distortion indicative of a fiber wrinkle within the composite laminate, wherein the analysis includes mapping the composite component by selecting a plurality of gate values corresponding to a plurality of depth locations within the composite laminate.

15. The system of claim 9, wherein the transmitter assembly is adapted to transmit an incident ultrasonic signal through a layer of liquid using at least one of an immersion tank, a squirter system, and a contact transducer.

16. A machine-readable medium including a computer program adapted to performing an ultrasonic inspection of a composite laminate, comprising:

a first portion adapted to receive a full waveform from each of a plurality of locations over an area of interest on the composite laminate;

a second portion adapted to store the full waveform at each of the plurality of locations over the area of interest; and a third portion adapted to analyze the full waveform at each of the plurality of locations over the area of interest for an amplitude distortion indicative of a fiber wrinkle within the composite laminate, wherein the analysis includes enabling the selection of a gate value corresponding to a depth location within the composite laminate and enabling the display of a C-scan image of an amplitude value from the full waveform at the plurality of locations over the area of interest, wherein the composite laminate further includes a back surface opposite from the front surface, and wherein receiving a full waveform at each of the plurality of locations over the area of interest includes receiving a full waveform of amplitude versus time between the front and back surfaces of the composite laminate at each of the plurality of locations over the area of interest.

17. The machine-readable medium of claim 16, wherein the first portion is adapted to receive a full waveform from each of a plurality of locations over an area of interest on the composite laminate in a pulse-echo mode of operation.

18. The machine-readable medium of claim 16, wherein the third portion is adapted to enable analysis of the full waveform at each of the plurality of locations over the area of interest for an amplitude distortion indicative of a fiber wrinkle within the composite laminate, wherein the analysis includes selectively adjusting a color palette range of the C-scan image over a baseline RF signal to capture amplitude differences of approximately a couple of dB.

19. The machine-readable medium of claim 16, wherein the third portion is adapted to enable analysis of the full waveform at each of the plurality of locations over the area of interest for an amplitude distortion indicative of a fiber wrinkle within the composite laminate, wherein the analysis includes mapping the composite component by selecting a plurality of gate values corresponding to a plurality of depth locations within the composite laminate.

* * * * *